(12) United States Patent
Servaites et al.

(10) Patent No.: US 7,248,357 B2
(45) Date of Patent: Jul. 24, 2007

(54) METHOD AND APPARATUS FOR OPTICALLY MEASURING THE HEATING VALUE OF A MULTI-COMPONENT FUEL GAS USING NIR ABSORPTION SPECTROSCOPY

(75) Inventors: James Servaites, Chicago, IL (US); Serguei Zelepouga, Hoffman Estates, IL (US)

(73) Assignee: Gas Technology Institute, Des Plaines, IL (US)

( * ) Notice: Subject to any disclaimer, the term of this patent is extended or adjusted under 35 U.S.C. 154(b) by 302 days.

(21) Appl. No.: 10/978,320

(22) Filed: Oct. 29, 2004

(65) Prior Publication Data

US 2006/0092423 A1    May 4, 2006

(51) Int. Cl.
 G01J 3/30 (2006.01)
 G01J 3/00 (2006.01)
 G01J 3/40 (2006.01)

(52) U.S. Cl. .................. 356/306; 356/300; 250/205; 374/100

(58) Field of Classification Search .............. 250/205; 356/306, 300, 305, 330; 374/100
 See application file for complete search history.

(56) References Cited

U.S. PATENT DOCUMENTS

| | | | |
|---|---|---|---|
| 3,950,101 A | | 4/1976 | Dewey, Jr. |
| 4,467,204 A | * | 8/1984 | Kysilka et al. .............. 250/343 |
| 4,553,032 A | * | 11/1985 | Lo et al. ................. 250/339.12 |
| 4,594,510 A | * | 6/1986 | Brown et al. .......... 250/339.13 |
| 4,849,637 A | * | 7/1989 | Cerff et al. .................. 250/345 |
| 4,958,076 A | | 9/1990 | Bonne et al. |
| 4,996,431 A | | 2/1991 | Bonne et al. |
| 5,717,209 A | | 2/1998 | Bigman et al. |
| 5,822,058 A | | 10/1998 | Adler-Golden et al. |
| 6,157,455 A | | 12/2000 | Pinvidic et al. |

(Continued)

FOREIGN PATENT DOCUMENTS

EP            81702 A1 *   6/1983

OTHER PUBLICATIONS

The Columbia Encyclopedia (2004). Retrieved Sep. 28, 2006, from xreferplus. http://www.xreferplus.com/entry/4294631.*

(Continued)

Primary Examiner—Layla G. Lauchman
Assistant Examiner—Scott M. Richey
(74) Attorney, Agent, or Firm—Mark E. Fejer

(57) ABSTRACT

A method and system for measuring heat energy of a combustible fluid in which light having wavelengths in the near-infrared is directed into a test cell containing the combustible fluid and portions of the light not absorbed by the combustible fluid and passing out of the cell are spatially dispersed by wavelength, forming a light spectrum that is projected onto a detector. The light spectrum is digitized and inputted into a data processing unit in which it is compared to the actual spectrum of the light source stored in the system to determine the absorbance spectrum of the combustible fluid. The system is spectrally calibrated by identifying known spectral features of the combustible gas absorbance spectrum. To correct for deviations in the original light source spectrum, a light source calibration system is employed. Upon determination of the absorbance spectrum of the combustible fluid, the heating value of the combustible fluid is determined by comparing the absorbance spectrum to a plurality of spectra located within an on-board database.

15 Claims, 6 Drawing Sheets

U.S. PATENT DOCUMENTS

| | | | |
|---|---|---|---|
| 6,396,056 B1 * | 5/2002 | Lord et al. | 250/252.1 |
| 6,490,908 B2 | 12/2002 | Schley | |
| 6,536,946 B1 | 3/2003 | Froelich et al. | |
| 6,555,820 B1 | 4/2003 | Tacke et al. | |
| 2005/0173635 A1 * | 8/2005 | Smith | 250/339.13 |

OTHER PUBLICATIONS

Brown, C.W., "Optical BTU Sensor Development", C. B. Analysis, Inc., Saunderstown, RI, Jul. 1993.

Brown, C.W. et al., "Novel Sampling Device for Obtaining Process Near-Infrared Spectra of High-Pressure Gases," Applied Spectroscopy, vol. 52, No. 5, 1998, 746-749.

Donahue, S. M. et al., "Near-Infrared Multicomponent Analysis in the Spectral and Fourier Domains; Energy Content of High-Pressure Natural Gas," Anal. Chem. 1988, 60, 1873-1878.

van Agthoven, M. A. et al., "Near-Infrared Spectral Analysis of Gas Mixtures", *Applied Spectroscopy*, vol. 56, No. 5 593-598 (2002).

Goldstein, N. et al., "Real-Time Optical BTU Measurement of Natural Gas at Line Pressure", 4th International Symposium on Fluid Flow Measurement, Jun. 27-30, 1999.

Sunshine, Steven A., "A Low Cost Optical Gas Composition Sensor", Natural Gas Quality & Energy Measurement X., Feb. 3-5, 1997, Kissimmee, FL. (GTI Electronic Symposium Proceedings), pp. 1-12.

Brown, C.W. et al., "Feasibility of On-line Monitoring of the BTU Content of Natural Gas with a Near-Infrared Fiber Optic System", Applied Spectroscopy, vol. 47, No. 6, 1993, 812-815.

\* cited by examiner

METHOD AND APPARATUS FOR OPTICALLY MEASURING THE HEATING VALUE OF A MULTI-COMPONENT FUEL GAS USING NIR ABSORPTION SPECTROSCOPY

BACKGROUND OF THE INVENTION

1. Field of the Invention

This invention relates to a method and apparatus for the measurement of a physical property of a fluid that is dependent upon a physical characteristic of at least one functional group and is related to the quantity of that functional group in the fluid. More particularly, this invention relates to the measurement of the heating value of a fuel gas at-line and in real time. Even more particularly, this invention relates to a method and apparatus for measuring the heating value of a combustible gaseous fuel mixture, including functional groups and molecules, using near infrared absorption spectroscopy.

2. Description of Related Art

Historically, the heat energy content of a combustible fluid was determined by burning precisely defined amounts of the fluid, e.g. natural gas, to determine the amount of energy produced from the combustion. Other methods determined the concentration of each whole combustible compound in the mixture, defining the energy content for each whole combustible compound, and summing them to yield the heat energy content of the entire mixture.

The heat energy content of natural gas flowing through a pipeline, which natural gas typically contains methane, ethane, propane and higher alkane hydrocarbons, frequently fluctuates, even over relatively short periods of time. Conventional methods of measurement generally require bypass flow-lines or fluid extraction to provide gas samples which are then taken to a lab and burned. The temperature of the flame is then measured. It is difficult to both continuously and accurately measure the energy content of natural gas in pipelines, and the lack of any convenient means for making such continuous and accurate measurements may result in improper charges during the course of a day to the disadvantage of both buyers and sellers.

Commercially, there are no known products capable of accurately determining the heating value of a fuel gas without removing a gas sample and reducing the sample pressure for analysis. Available sensors are primarily comprised of calorimeters and gas chromatographs (GCs). However, such devices, in addition to requiring the removal of samples from pipelines, have slow response times, and have high initial and maintenance costs.

One technique for addressing the need for both continuous and accurate measurement of the heat energy content of combustible gaseous fluid mixtures employs infrared spectroscopy in which infrared radiation causes groups of atoms of organic compounds to vibrate about their covalent bonds. Because of the vibrations, the groups of atoms absorb a quantified amount of infrared energy in particular regions of the spectrum. U.S. Pat. No. 4,594,510 to Brown et al. teaches a heat energy measuring system which directs radiation through a sample of a combustible fluid and detects the absorbance of at least one combustible component of the combustible fluid at a selected spectral line, where there is at least one spectral line for each combustible component to be examined in the fluid. The system also combines at least one heat energy proportionality factor with the absorbance at each spectral line and sums these combinations to determine the heat energy of the fluid. Calibration for specific hydrocarbon species is achieved with an on-board system of individual cells of gases from which calibration matrices are calculated. This method of calibration disadvantageously adds a significant amount of time and complexity to the system.

U.S. Pat. No. 5,822,058 to Adler-Golden et al. teaches the use of absorption spectroscopy to derive the heat of combustion of a combustible mixture. The absorption spectrum is measured by utilizing a light source, light dispersing device, and a detector. However, the heat of combustion is not measured directly. Rather, the mixture composition is first determined from which the heat of combustion is derived by relating individual hydrocarbon heats of combustion. The '058 patent further teaches the use of absorption spectra of natural gas over the wavelength range of about 700-1000 nm. The detector is a silicon detector which cannot be used to detect wavelengths higher than about 1000 nm. Light source degradation is addressed by allowing a second fiber-optic cable from the light source to be directed straight to the spectrometer and then to the detector. This is able to be accomplished because a 2D detector is used. This larger detector has more surface area, thereby allowing for a second spectrum to be analyzed.

U.S. Pat. No. 6,555,820 B1 to Tacke et al. teaches a photometric device and method for determining the gross calorific value of natural gas having a radiation source that produces a measuring beam and a modulation unit to modulate a measuring beam. A test cell with a test gas and a receiver for the beam are arranged successively in the path of the measuring beam. The measuring signals of the receiver are supplied to an evaluation unit that includes at least one signal amplifier for amplification of the signals. The gross calorific value of the gas is indicated by the sum of the amplified measuring signals produced in a computing machine. However, no means are provided for tracking the fluctuations or degradation of the light source spectrum, which fluctuations or degradation may constitute a large source of error when calculating gas energy content.

SUMMARY OF THE INVENTION

Accordingly, it is one object of this invention to provide a method and system for measuring the heating value of a fuel gas at-line and in real-time.

It is another object of this invention to provide a method and system for measuring the heating value of a fuel gas which embodies quick response times, on the order of less than about 5 seconds, while maintaining initial costs as well as maintenance costs low.

It is another object of this invention to provide a method and system capable of continuous measurement of the heating value of a fuel gas.

It is yet a further object of this invention to provide a method and system for measuring the heating value of a fuel gas using absorption spectroscopy which addresses the potential problems associated with instability and/or degradation of the light source.

These and other objects of this invention are addressed by a method and system for measuring the heat energy of a combustible fluid in which radiation means direct radiation through a sample of the combustible fluid, detection means detect the absorbance of at least one combustible component of the combustible fluid at a selected spectral line, where there is at least one spectral line for each combustible component to be considered in the combustible fluid, calibration means calibrate the source of the radiation, storage means store a plurality of spectra of combustible gas mixtures, thereby enabling comparison of the measured absorbance spectrum to the plurality of spectra, combination means combine at least one heat energy proportional factor with the absorbance at each spectral line, and summing means sum the combinations to determine the heat energy of the combustible fluid.

The system of this invention continuously acquires absorption spectra from gases in the near-infrared region. The near-infrared region of the electromagnetic spectrum is particularly useful because combustible gas components, in particular methane, ethane, propane, butane, iso-butane, and hexane produce strong absorbent spectra in this spectral range.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1:
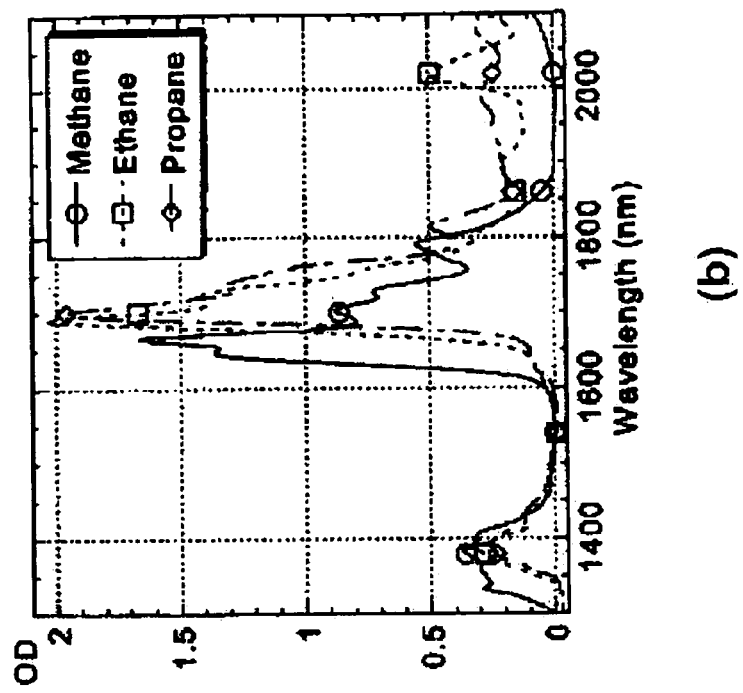
FIG. 1 shows examples of absorption spectra for individual mixture components of combustible gas mixtures.
Figure 1:
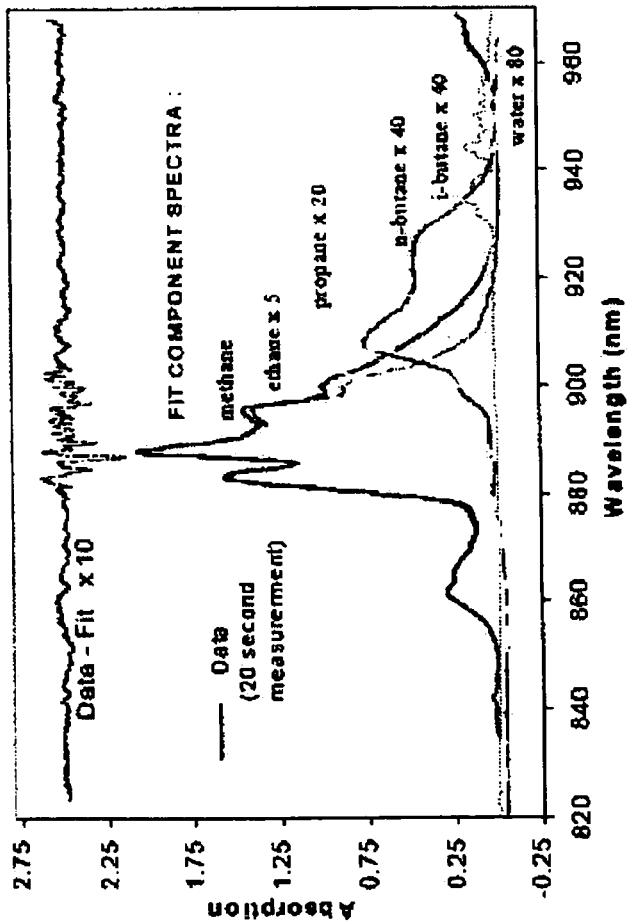

The invention claimed herein is a method and system for measuring the heating value of a combustible fluid, such as natural gas, containing a plurality of combustible components. The invention utilizes the relationship between absorption spectroscopy and heating value and/or composition of a gas mixture which enables the quick, accurate and cost-effective relay of information to the user. As previously indicated, the absorbance spectra of combustible fluids can be converted into usable properties such as heating value and/or composition. The system of this invention continuously acquires absorption spectra from gases in the near-infrared region. FIG. 1 shows two plots exhibiting the absorption spectra of several natural gas components at different near-infrared spectral regions. The plot on the left (a) (Goldstein et al., "Real-Time Optical BTU Measurement of Natural Gas at Line Pressure," 4th International Symposium on Fluid Flow Measurement, Jun. 27-30, 1999) displays several individual components of the combined spectrum over the range of 820-960 nm while the plot on the right (b) (Van Agthoven, M. A., "Near-Infrared Spectral Analysis of Gas Mixtures," *Applied Spectroscopy*, 56, 593, No. 5, 2002) shows individual absorption spectra for methane, ethane and propane over the range of 1300-2100 nm. Other near-infrared and infrared spectral regions exist where combustible fluid components exhibit absorption spectra as well.

The absorption spectrum of a gas mixture is measured and the absorbance spectrum is calculated through a multi-step process. First, the light source permeates the gas, causing spectral regions of the light to become absorbed by the gas mixture, effectively elevating the gas molecules to higher quantum energy levels. The data processing unit processes this modified light spectrum resulting in an absorbance spectrum of the gas mixture. Simply put, this is calculated using the following equation:

$$A = -\ln(I/I_0) \qquad (1)$$

where A is the absorbance, I is the intensity of the light passed through the gas mixture, and $I_0$ is the intensity of the original light source. When this equation is applied to each wavelength observed, a full absorbance spectrum is obtained. This absorbance can be correlated to the gas mixture physical properties through the well-known Beer's law, which is usually expressed as:

$$A = a \cdot l \cdot c \qquad (2)$$

where A is the absorbance, a is the inherent absorptivity, l is the distance that the light travels through the gas mixture, and c is the concentration. The product of the inherent absorptivity and the path length can be expressed as a proportionality constant, k. For a mixture with several components contributing to the absorbance, a series of equations can be used for calculations:

$$[A_1 A_2 \cdots A_N] = [c_1 c_2 \cdots c_j] \begin{bmatrix} k_{11} & k_{12} & \cdots & k_{1N} \\ k_{21} & k_{22} & \cdots & k_{2N} \\ \vdots & \vdots & & \vdots \\ k_{j1} & k_{j2} & \cdots & k_{Nj} \end{bmatrix} \qquad (3)$$

where A are the absorbance values at discrete wavelengths, c are the concentrations of the components, and k are the proportionality constants. Inversing this equation gives a method for calculating the concentrations:

$$[c_1 c_2 \cdots c_j] = [A_1 A_2 \cdots A_N] \begin{bmatrix} p_{11} & p_{12} & \cdots & p_{1j} \\ p_{21} & p_{22} & \cdots & p_{2j} \\ \vdots & \vdots & & \vdots \\ p_{N1} & p_{N2} & \cdots & p_{Nj} \end{bmatrix} \qquad (4)$$

where p are proportionality constants. The matrix containing the proportionality constants (P-matrix) is known as the calibration matrix for determining the mixture composition. The determination of the calibration matrices can be performed using one of several different algorithms. Some examples of suitable algorithms are Principal Component Regression (PCR), Partial Least Squares (PLS), and Partial Least Squares II (PLS2). These data analysis algorithms are well-known to those skilled in the art.

The matrix equations above describe a method to derive the mixture concentrations. The following equation can be used to relate the mixture concentrations to the heating value of the gas mixture:

$$HV = 1/R \cdot T \cdot p/z \Sigma X_n \cdot H_n \qquad (5)$$

where R is the ideal gas constant, T is the mixture temperature, p is the total pressure, z is the compressibility factor of he mixture, $X_n$ is the component mole fraction, and $H_n$ is the component heat of combustion. Because the heating value is proportional to the mixture composition, equation 4 can be rewritten for determining the mixture heating value as:

$$[h_1 h_2 \cdots h_j] = [A_1 A_2 \cdots A_N] \begin{bmatrix} p'_{11} & p'_{12} & \cdots & p'_{1j} \\ p'_{21} & p'_{22} & \cdots & p'_{2j} \\ \vdots & \vdots & & \vdots \\ p'_{N1} & p'_{N2} & \cdots & p'_{Nj} \end{bmatrix} \quad (6)$$

where h are the heats of combustion for the different mixture components and p' are proportionality constants for determining the mixture heating value. This P'-matrix is calculated independently of the P-matrix used previously, again using an algorithm such as PCR, PLS, or PLS2.

Figure 2:
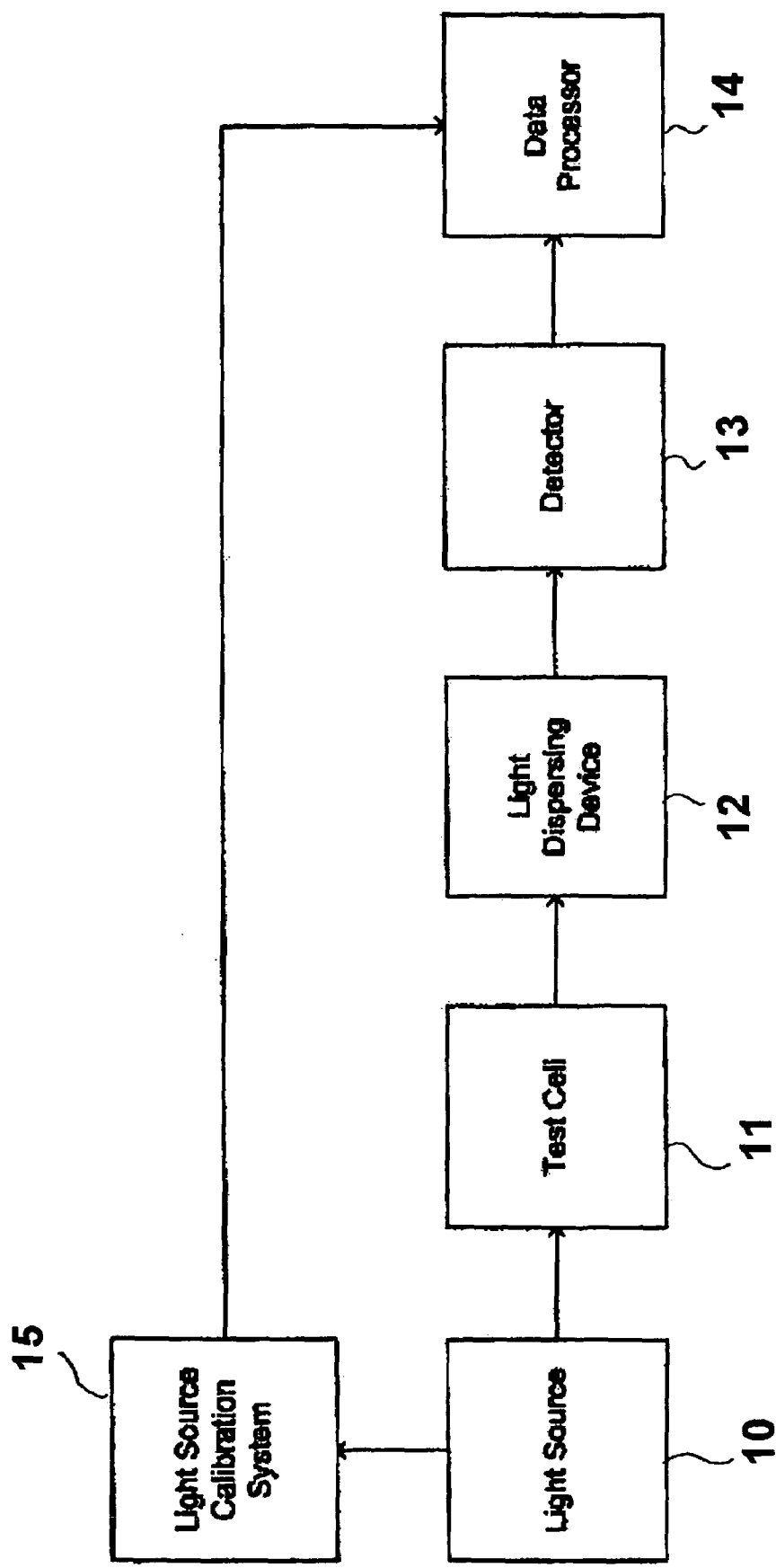
FIG. 2 is a block diagram showing the light path within the heating value sensing system in accordance with one embodiment of this invention.

FIG. 2 is a block diagram showing the basic method and system of this invention. The system comprises a light source 10 which produces an output spectrum which includes near-infrared light, a test cell or gas cell 11 adapted to receive light from the light source 10, a light dispersing device 12 having a light inlet side and a dispersed light outlet side, a light dispersing device 12 adapted to receive light transmitted through test cell 11 and to spatially disperse the light received from the test cell, a detector 13 adapted to detect the dispersed light produced by the light dispersing device 12, a data processor 14 adapted to receive and process a data signal produced by detector 13, and a light source calibration system 15 adapted to receive light from light source 10 and transmit a data signal to data processor 14. The light dispersing device can be any instrument capable of dispersing light spectrally. Examples include spectrometers, prisms, and interferometers. The detector receiving the dispersed light can be any detector capable of sensing near-infrared light, such as an InGaAs detector.

In operation, as the light from light source 10 passes through the test cell 11, the gas within test cell 11 absorbs a spectrum of light corresponding to the composition, temperature, and pressure of the gas mixture present. The light then passes to the light dispersing device 12 which disperses the light spatially by wavelength and projects the light spectrum onto the detector 13 in which the spectrum is digitized. The digitized spectrum is then transmitted into the data processing unit 14.

Concurrent with the process described above, a light source calibration system 15 receives light from the light source 10, after which it communicates data to the data processing unit 14 as shown in FIG. 2. This calibration system serves to measure the stability of the light source spectrum, which may vary over time. All data transferred to the data processing unit are processed in real time.

Figure 3:
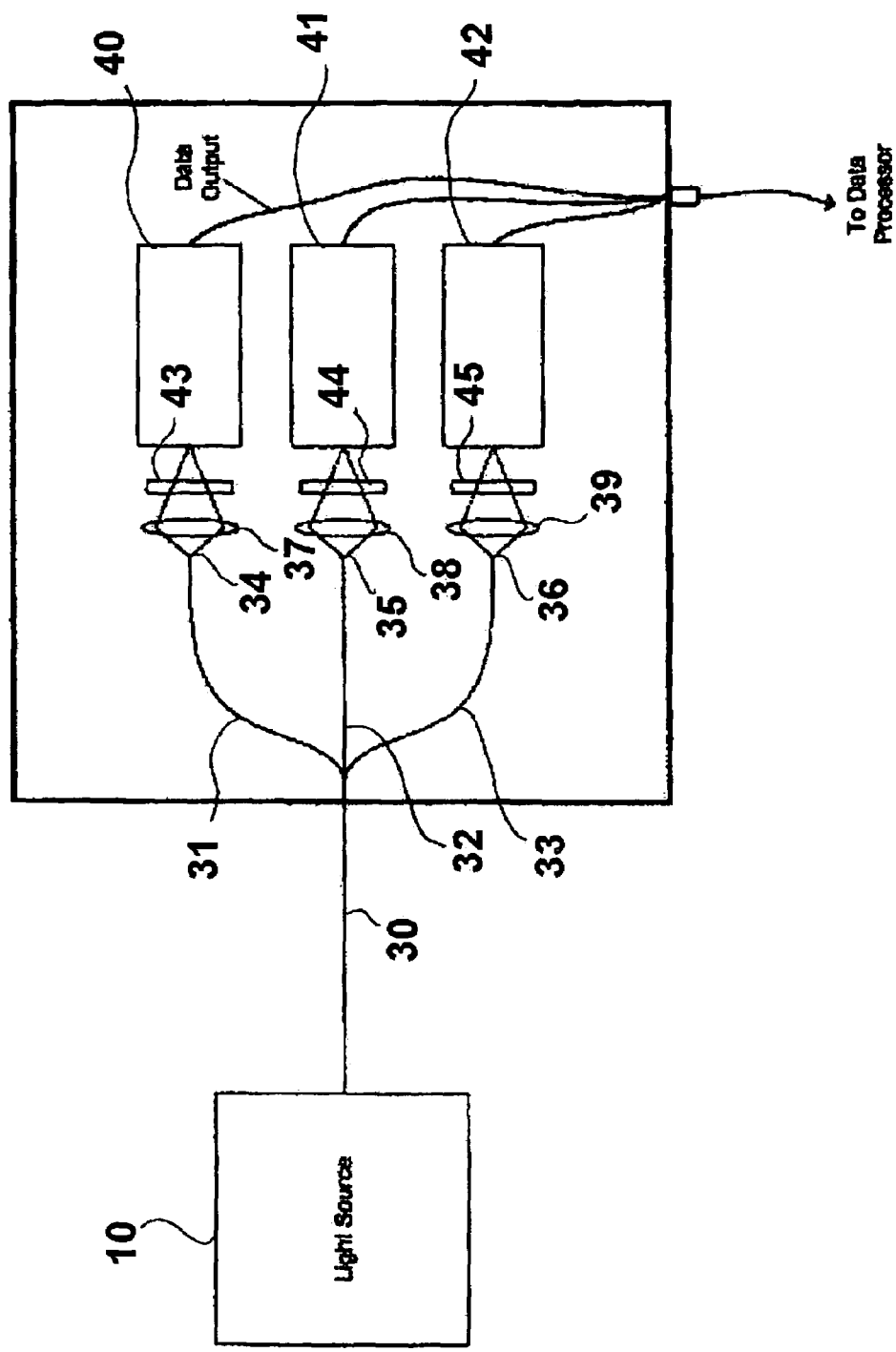
FIG. 3 is a diagram showing the light source calibration system utilized in the heating value sensing system in accordance with one embodiment of this invention.

Light source calibration system 15, shown in accordance with one embodiment of this invention in FIG. 3, comprises at least two transmitting means for transmitting light from light source 10 to the light calibration system. In the embodiment shown in FIG. 3, the light is transmitted from light source 10 through a fiber-optic bundle 30, which is then split into two or more smaller fiber-optic cables or bundles 31, 32, 33 having light output ends 34, 35, 36. Disposed at light output ends 34, 35, 36 are focusing lenses 37, 38, 39 by which the light transmitted through the fiber-optic cables is focused on to detectors 40, 41, 42 of an infrared-sensitive photodiode. Disposed between the lenses 37, 38, 39 and detectors 40, 41, 42 is a narrow band interference filter 43, 44, 45, which filter is different for each light path. Each filter has a center wavelength over the absorption spectral range of the gas mixture. The full width half maximum (FWHM) of the filters is dependent on the spectral range being analyzed, but 10 nm is generally considered to be a good value. The intensity of the filtered light signals are then converted to digital signals through the near-infrared-sensitive photodiode, which digital signals are then transmitted to the data processing unit 14.

Figure 4:
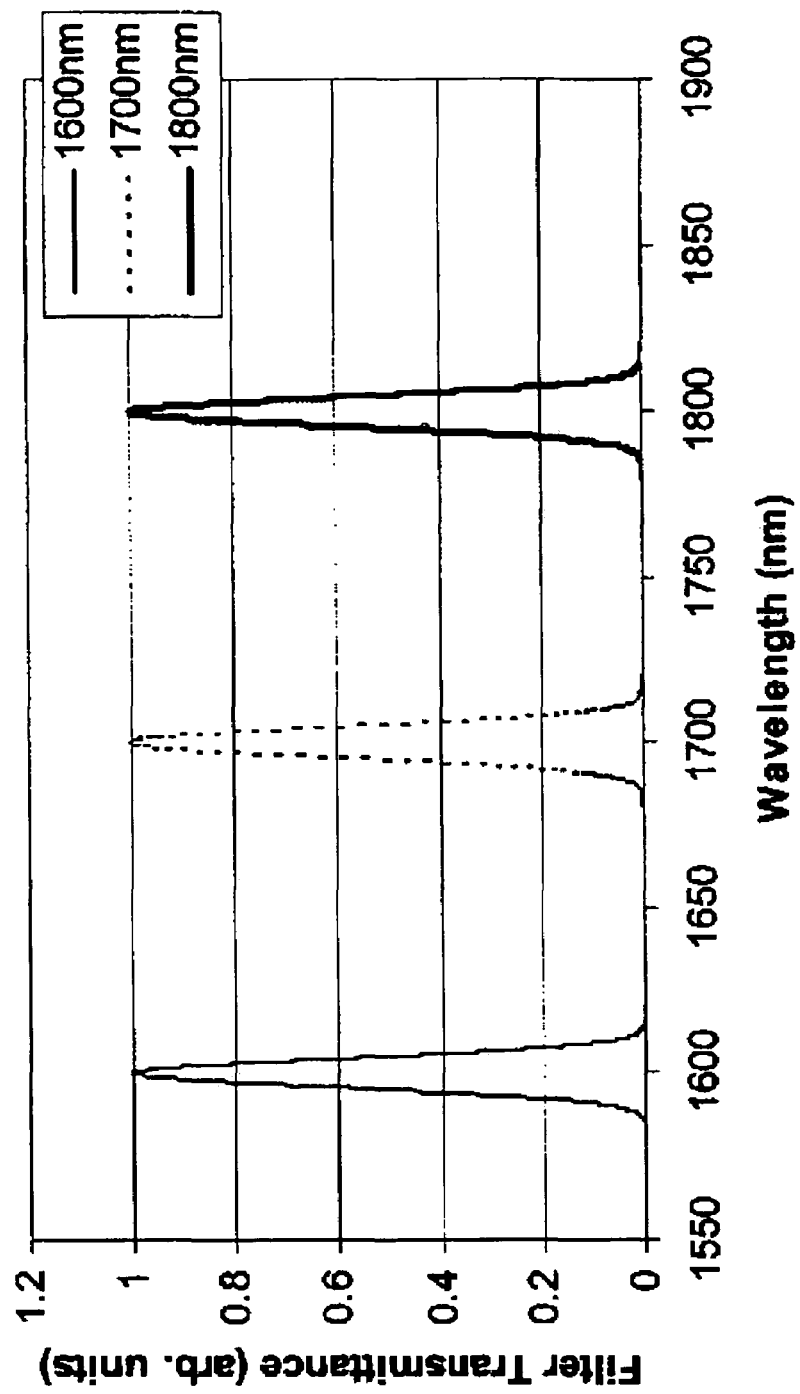
FIG. 4 is a diagram of exemplary light source calibration filter profiles generated in accordance with the method of this invention.
Figure 5:
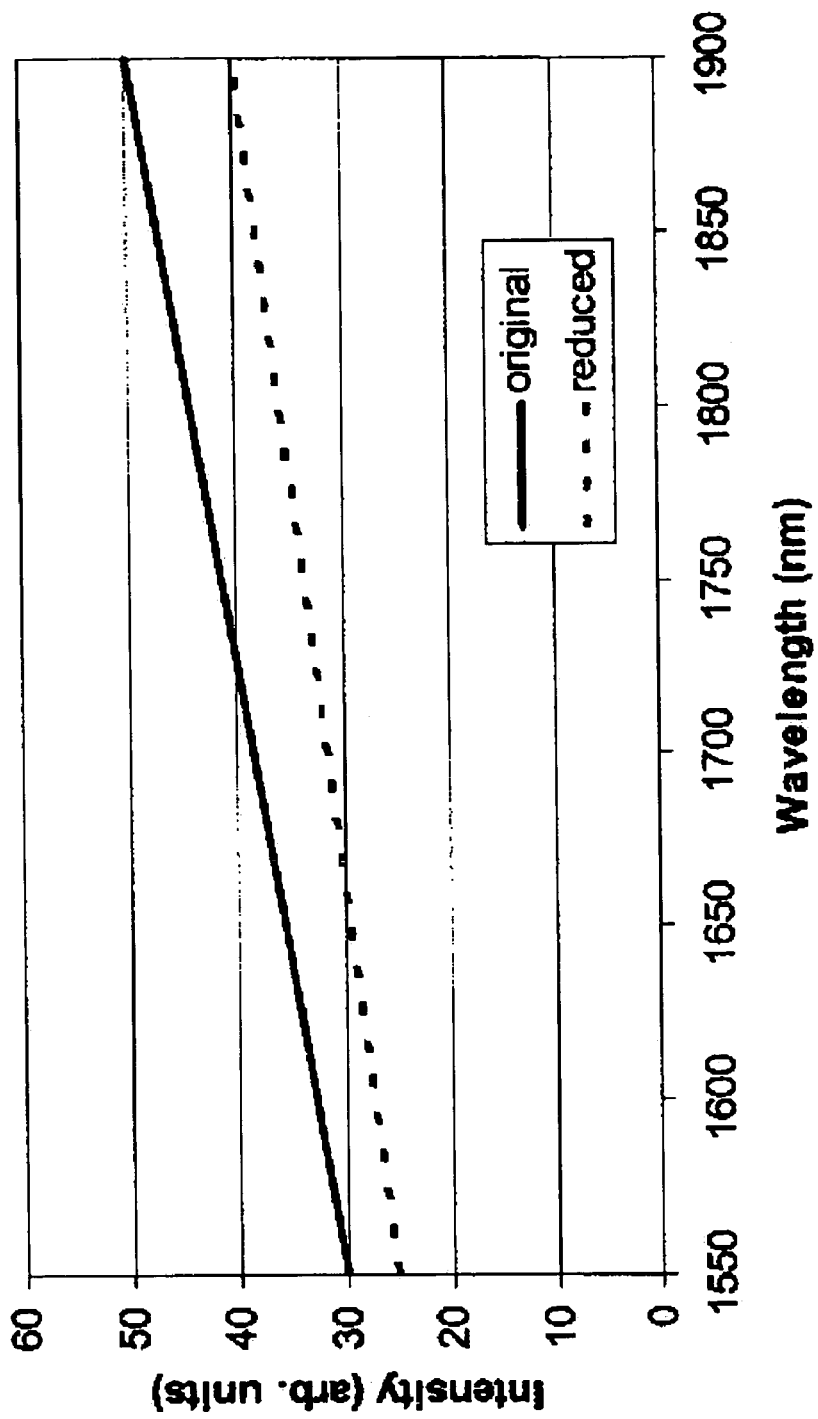
FIG. 5 is a diagram of exemplary original light source and reduced light source profiles generated in accordance with the method of this invention.

FIG. 4 shows three exemplary filter profiles that could be used for a near-infrared light source, and FIG. 5 shows an exemplary pseudo light source intensity spectrum and the same spectrum that is slightly changed, i.e. reduced. The reduced spectrum corresponds to the original light source, but is slightly reduced due to extensive use of the light source. The filter profiles shown in FIG. 4 fall within the same range as the region of interest of the light source, in the example shown, between 1550 and 1900 nm. When the light from the source passes through each of these filters, the actual intensity of the light at each of the three wavelength, in the example shown, 1600, 1700, and 1800 nm, can be deduced by dividing the intensity by the integral of the filter profile. This can only be done if the filter profile is assumed to be linear over the range of the filter, which is most often the case over a short span. From the known intensity points of the light source, the actual light source spectrum over the region of interest can be calculated by sliding the original spectral curve down to coincide with the known data points. From here, future calculations made with the sensor can be compensated for the degraded light source spectrum. The light source spectrum calibration is very important to the overall sensor because an uncompensated change in this spectrum can result in large percentage errors when calculating the heating value of a combustible fluid.

Figure 6:
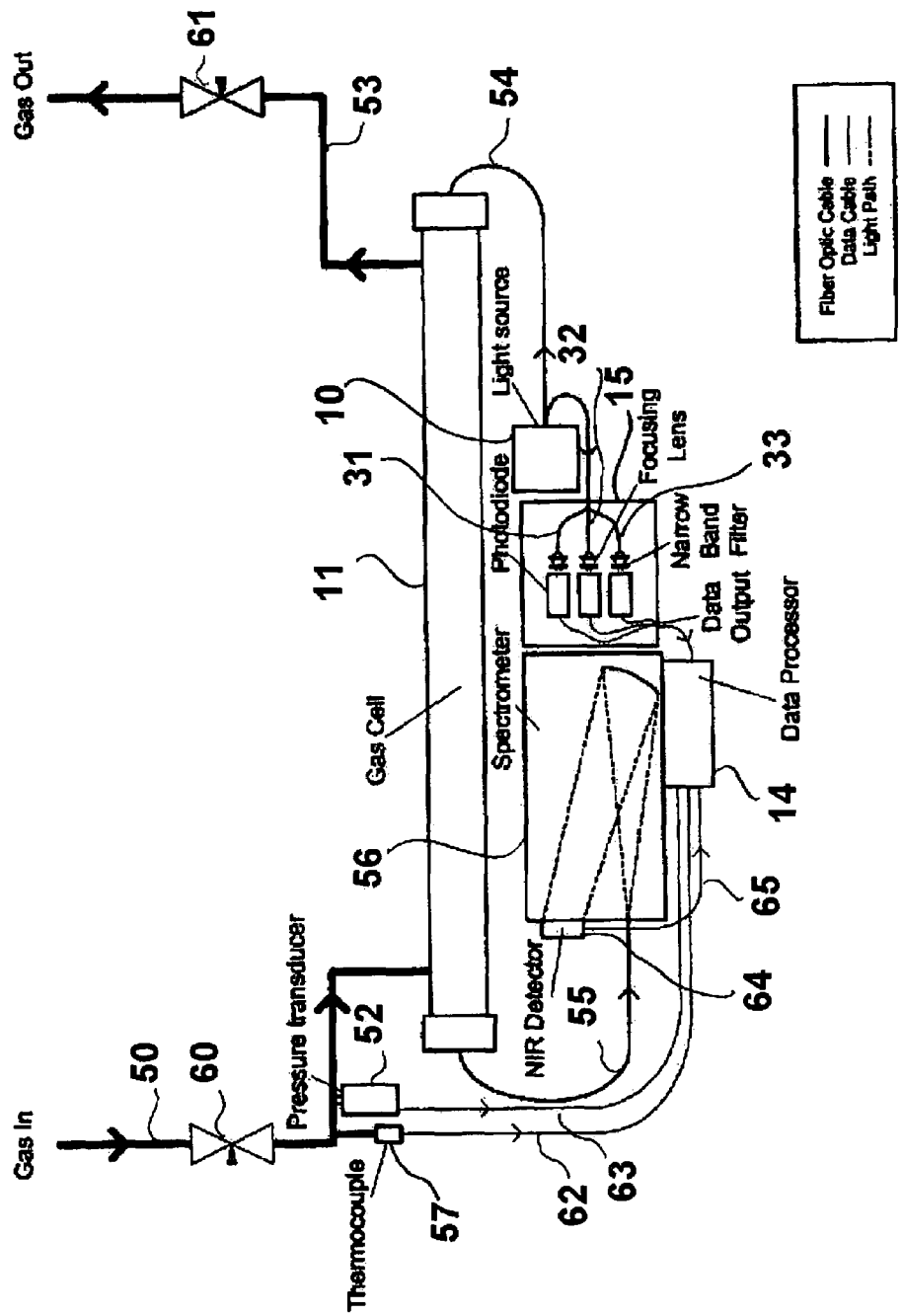
FIG. 6 is a diagram of a system for measuring the heat energy of the combustible fluid in accordance with one embodiment of this invention.

FIG. 6 shows a complete system for optically measuring the heating value of a multi-component combustible fluid in accordance with one embodiment of this invention. The system comprises gas inlet control means for controlling the flow of combustible gaseous fluid into and through gas cell 11. In accordance with the embodiment shown in FIG. 6, said gas inlet control means comprises a valve 60. The system further comprises at least one temperature sensor 57 and at least one pressure sensor 52 adapted to monitor the temperature and pressure of the combustible gaseous fluid entering gas cell 11. To provide for continuous flow of the combustible gaseous fluid through gas cell 11, the system further comprises gas outlet control means for controlling the flow of combustible gaseous fluid out of gas cell 11. In accordance with the embodiment shown in FIG. 6, said gas outlet control means comprises a valve 61.

In operation, a combustible gas mixture is introduced by means of line 50 through valve 60 into gas cell 11. Temperature sensor 51 and high-speed pressure transducer 52, operably connected to line 50, monitor the inlet gas mixture conditions. The data acquired from these sensors is transmitted by means of data transmission lines 62 and 63 directly to the data processing unit 14 for use in calculations. The gas mixture continuously flows through the gas cell 11 and out of the cell through line 53 and valve 61. As the gas is flowing through the cell, near infrared light provided by light source 10 is transmitted by means of a fiber-optic bundle 54 into the gas cell. Another fiber-optic bundle 55 accepts the light transmitted through the gas cell and transmits it to a spectrometer 56 in which the light is dispersed and the resulting spectrum projected on to an extended near-infrared detector 64. This detector is capable of detecting light in the range of about 0.9-2.5 µm. The spectrum data is then transmitted by means of data transmission line 65 to data processor 14.

Concurrent with this process, light is transmitted from the light source 10 to the light source calibration system 15 in which the transmitted light is split into three separate paths by means of three fiber-optic bundles 31, 32, 33, each of which transmits the light through a focusing lens, through a narrowband interference filter, and on to an extended InGaAs photo diode. Each of the three filters has a full width at half maximum of 10 nm and the filter center wavelengths are 1.6, 1.7 and 1.8 μm. The light intensity at each wavelength is compared to the stored original intensity at each wavelength and then the data processor computes the adjusted light source spectrum. The corrected light source spectrum is compared to the light spectrum transmitted through the gas sample to calculate the gas mixture spectral absorbance. Using the calculated absorbance spectrum, the gas composition mixture and the mixture heating value are calculated. These data are written to a data file and also displayed on a screen for observation by an operator.

In accordance with one embodiment of the method of this invention, light emitted from a light source, which includes near-infrared light, 1100 to 1900 nm, is transmitted by means of a fiber-optic cable, or other practical means, to a gas cell. The test cell has mounted to it a pressure transducer and a temperature sensor, data from which is transmitted to an on-board data processing unit. The test cell, containing a mixture of one or more combustible gases, has an optical entrance window allowing near-infrared light to pass into the cell. The gas mixture can either be continuously passing through the test cell, as would be the case in a gas pipeline, or it can be a static sample entered into the cell by a user. As the light passes through the gas mixture within the cell, spectrum information is absorbed by the gas mixture. The light exits the gas cell through the same port as the entrance after reflecting off of one or more mirrors within the cell or simply by passing through a window on the opposite side of the gas cell. Upon exiting the gas cell, the light is then transferred by means of a fiber-optic cable or other practical means to a light-resolving device having a coupled detector with sensitivity in the near-infrared. The light-resolving device can be a grating spectrometer, interferometer, or similar devices. The detector can be any 1D or 2D near-infrared-sensitive detector capable of transmitting a digital signal. The digital light spectrum exiting the detector is then transferred to the on-board data processing unit.

Concurrently, light emitted from the light source is transmitted by means of a fiber-optic cable or other practical means to a light source calibration system, an on-board device capable of determining the stability and spectral changes of the light source. The system contains two or more filtered photo diodes which accept light from the light source. The filter center wavelengths fall in the near-infrared spectral region where absorption spectral features of interest of the gas mixture are located, within the range of about 1500 to about 1900 nm. The exact filter transmission characteristics are programmed into the data processing unit. Upon receiving light from the light source, the filtered light intensities are converted into actual intensity points of the light source spectrum by the data processing unit. These two or more data points are then used to decipher the light source spectrum integrity by comparing the values to those of the original light source spectrum.

The data processing unit continuously calculates the absorption spectrum of the combustible gas mixture using the first equation set forth herein above. This equation is processed in a matrix format and is applied to each wavelength, more specifically, each pixel of the detector, acquired by the spectral-resolving device/detector. From here, the mixture heating value and/or the gas mixture composition is calculated using equations 4 and 6 herein above. The heating value and/or gas composition data calculated by the data processing unit are then output to a local or remote display and/or control system.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A system for measuring heat energy of a combustible fluid, the system comprising:
   radiation means for directing radiation through a sample of said combustible fluid;
   detection means for detecting an absorbance of at least one combustible component of said combustible fluid at a selected spectral line, there being at least one said spectral line for each said combustible component to be considered in said combustible fluid;
   a data processor comprising storage means for storing a plurality of spectra of combustible gas mixtures and for comparing said plurality of spectra to a measured absorbance spectrum, combination means for combining at least one heat energy proportional factor with said absorbance at each said spectral line, and summing means for summing said combinations to determine said heat energy of said combustible fluid; and
   calibration means for calibrating a source of said radiation, said calibration means comprising at least two focusing lenses, at least two light intensity detectors adapted to provide an output signal to said data processor, each said light intensity detector linearly aligned with one of said focusing lenses, and at least one narrow band interference filter disposed between, and linearly aligned with, each of said focusing lenses and said light intensity detectors.

2. A system in accordance with claim 1, wherein said spectral lines are in a range of about 1100 nm to about 1900 nm.

3. A system in accordance with claim 1, wherein said radiation means comprises at least one light source selected from the group consisting of an incandescent lamp, at least one light emitting diode, and combinations thereof.

4. A system in accordance with claim 3, wherein said detection means comprises at least one gas cell suitable for containing said sample of combustible fluid, said at least one gas cell in optical communication with said at least one light source.

5. A system in accordance with claim 4, wherein said optical communication comprises at least one optical fiber bundle extending between said at least one light source and said at least one gas cell.

6. A system in accordance with claim 4, wherein said radiation means further comprises at least one light dispersing element disposed between said at least one gas cell and said detection means, said at least one light dispersing element adapted to disperse light transmitted from said at least one gase cell to said detection means.

7. A system in accordance with claim 6, wherein said optical communication comprises at least one optical fiber bundle extending between said at least one light dispersing element and said at least one gas cell.

8. A system in accordance with claim 4 further comprising temperature sensor means for measuring a gas temperature in said at least one gas cell.

9. A system in accordance with claim 8 further comprising pressure sensor means for measuring a gas pressure in said at least one gas cell.

10. A system in accordance with claim 1, wherein said detection means comprises at least one of a photo diode array detector and a photo conductor array detector, said detectors being sensitive to wavelengths in a range of about 1100 nm to about 1900 nm.

11. A system in accordance with claim 6, wherein said at least one light dispersing element is selected from the group consisting of a spectrometer, a prism, and an interferometer.

12. A system in accordance with claim 1, wherein said focusing lenses are composed of a material permeable to light having wavelengths in a range of about 1100 nm to about 1900 nm.

13. A system in accordance with claim 1, wherein said narrowband interference filters have center wavelengths in range of about 1100 nm to about 1900 nm.

14. A system in accordance with claim 1, wherein said light intensity detectors are photodiode detectors sensitive over a wavelength range of about 1100 nm to about 1900 nm.

15. A system in accordance with claim 1, wherein said light intensity detectors are photo conductor detectors sensitive over a wavelength range of about 1100 nm to about 1900 nm.

* * * * *